US007282485B2

(12) United States Patent
Beljanin et al.

(10) Patent No.: US 7,282,485 B2
(45) Date of Patent: Oct. 16, 2007

(54) METHOD OF OBTAINING D-GLUCURONIC ACID

(75) Inventors: Maksim Lvovich Beljanin, Tomsk (RU); Evgeniy Danilovich Goldberg, Tomsk (RU); Alexandr Michailovich Dygai, Tomsk (RU); Viktor Dmitrievich Filimonov, Tomsk (RU); Veniamin Abramovich Khazanov, Tomsk (RU)

(73) Assignee: Obschestvo S Ogranichennoi Otvetstvennoctiyu "Macferon", Moscow (RU)

( * ) Notice: Subject to any disclaimer, the term of this patent is extended or adjusted under 35 U.S.C. 154(b) by 236 days.

(21) Appl. No.: 10/956,474

(22) Filed: Oct. 1, 2004

(65) Prior Publication Data

US 2005/0113313 A1 May 26, 2005

(30) Foreign Application Priority Data

Apr. 2, 2002 (RU) .............................. 2002108340
Dec. 20, 2002 (RU) ..................... PCT/RU02/00542

(51) Int. Cl.
*A61K 31/70* (2006.01)

(52) U.S. Cl. ......................................... 514/23; 536/124

(58) Field of Classification Search .................. 514/23; 536/124

See application file for complete search history.

(56) References Cited

FOREIGN PATENT DOCUMENTS

GB 670928 4/1952

OTHER PUBLICATIONS

Rist, C. E. et a,l J. Am. Chem. Soc. 1951, 73, 2424-27.*
Hawley's Condensed Chemical Dictionary, 1997, p. 426.*
Israelstam et al J.Org. Chem. 1961, 26, 240-242.*
C.L. Mehltretter et al., "A Practical Synthesis of D-Glucuronic Acid through the Catalytic Oxidation of 1,2-Isopropylidene-D-glucose", J. Am. Chem. Soc., 1951, V. 73, No. 6, pp. 2424-2427.

* cited by examiner

*Primary Examiner*—Leigh C. Maier
*Assistant Examiner*—Ganapathy Krishnan
(74) *Attorney, Agent, or Firm*—Pauley Petersen & Erickson

(57) ABSTRACT

A method of obtaining D-glucuronic acid. The D-glucuronic acid and its derivatives (lactone, salts, amides, etc.) are biologically high-active compounds, which are widely used in medicine and pharmaceutical chemistry for the synthesis of modified drugs as well as used as food additives, skin-care preparations, and the like. This invention provides an environmentally friendly method of obtaining D-glucuronic acid which has widespread operational possibilities. The D-glucuronic acid is obtained by heating the salts of 1,2-0-isopropylidene-D-glucuronic acid in a water-containing solution in the presence of an acid agent, for which sulphonic acid cation exchanger resins are used.

4 Claims, No Drawings

METHOD OF OBTAINING D-GLUCURONIC ACID

BACKGROUND OF THE INVENTION

1. Field of the Invention

This invention relates to a method of obtaining D-glucuronic acid. D-glucuronic acid and its derivatives (lactone, salts, amides, etc.) are biologically high-active compounds, which are widely used in medicine and pharmaceutical chemistry for the synthesis of modified drugs as well as food additives, skin-care preparations, and the like.

2. Discussion of Related Art

Most methods of obtaining D-glucuronic acid are based on 1,2-isopropylidene-D-glucose, during the oxidation of which 1,2-isopropylidene-D-glucuronic acid, or frequently the salts thereof (Na, K, Ca, Ba, etc.), is or are precipitated. The following steps are used to convert these compounds into glucuronic acid:

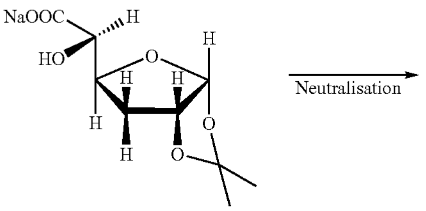

Na-JPGK

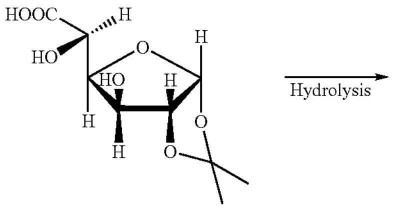

JPGK

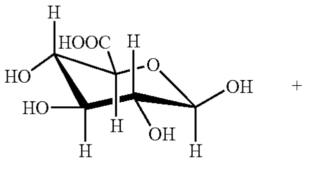

D-glucoronic acid

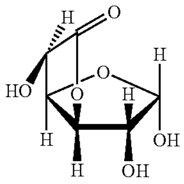

D-glucoren

Glucuronic acid is distinguished for its high chemical instability and is suitable for many conversions under mild conditions. The tautomeric conversions into solutions (mutarotation), typical for monosaccharides, are more difficult with glucuronic acid because of the formation of D-glucofuranyrone-6,3-lactone (glucuronic acid lactone). The equilibrium ratio of the components at room temperature is 60% glucuronic acid and 40% glucuronic acid lactone. The increase in temperature and the presence of acid catalysts accelerate achieving this equilibrium. When heating D-glucuronic acid in the presence of strong acids, the decarboxylation also occurs easily with the formation of carbon dioxide, furfural and other products of decomposition. In the acidic, neutral and alkaline media, the glucuronic acid is converted into epimers according to C-2 and also into the respective ketonic acids and isomeric GK-aldehyde acids. This makes the processes for obtaining glucuronic acid (GS) more difficult and causes, in known methods, either the mixtures of GS or the salts of glucurone (GK) to be obtained.

A method of obtaining 1,2-isopropylidene-D-sodium glucuronate is known, for example from USSR No. 883054 M.Kl.[3] C07H7/02 which is used as the intermediate product during the synthesis of D-glucuronic acid, the lactones thereof (glucurone) and the derivatives thereof, which are obtained by a catalytic oxidation of 1,2-isopropylidene-D-glucose with air oxygen in the weakly basic medium at a high temperature and by agitation. During the oxidation, the catalyst used is a palladium catalyst, which has 1.8% Pd relative to carbon, conveyed through potassium salts (0.8%) and sodium salts (0.2%) at a ratio between the compound to be oxidized and the catalyst of 1:0.45-0.91 at a temperature of 65-70° C., at a pH value of 7.5-8.0 and at a concentration of the starting substance of 1-10%.

However, D-glucuronic acid and glucuronic lactone cannot be obtained with this known method.

Another method of obtaining D-glucuronic acid is known from Mehltretter C. L., Alexander B. H., Mellies R. L. et al. “A Practical Synthesis of D-Glucuronic Acid through the Catalytic Oxidation of 1,2-isopropylidene-D-glucose”, J. Am. Chem. Soc., 1951, V. 73, No. 6, Pages 2424-2427. In this method, the water solution of Ca-isopropylidene glucuronic acid is heated at a temperature of 90-100° C. with an equimolecular quantity of the dihydrate of oxalic acid during a time period of 1.75 hours, and then the insoluble and precipitated calcium oxalate is filtered. After the removal of the water and after the reaction mass has been treated with ethanol, a mixture is obtained which contains 60% glucuronic acid and 40% glucuronic acid lactone (GK lactone).

This method has only limited operational possibilities, because it can only be used for calcium salts, or barium salts, of 1,2-0-isopropylidene-D-glucuronic acid, the neutralization and hydrolysis of which lead to insoluble calcium or barium oxalates, which can easily be separated from the GK solution and the GK lactone by filtering. The other salts of 1,2-0-isopropylidene-D-glucuronic acid, such as sodium or potassium, provide soluble oxalates which cannot be separated from the target product by the known methods.

One invention of particular relevance to the technical essence and to the object to be achieved with this invention is a method of obtaining D-glucuronic acid which is precipitated in the form of an Na salt, as taught by Feldmann D. P., Woytenko A. D., Shimaskaya M. B., etc. “Verfahren zur Gewinnung von D-Natriumglukuronat” [in translation: “Method of obtaining D-sodium glucuronate”], Chemie-Pharm. Magazin, 1984, No. 11, Pages 1356-1360. In this known method, the acetonation of the D-glucose is accomplished in the presence of sulphuric acid by forming a mixture of two principal products, namely 1,2-0-isopropylidene-D-glucuronic acid and 1,2;5,6-di-O-isopropylidene-D-glucuronic acid, the last compound being converted by an acid hydrolysis into 1,2-O-isopropylidene-D-glucose, and 1,2-O-isopropylidene-D-sodium glucuronate being obtained by the catalytic oxidation thereof. By the hydrolysis of such compound by heating to a temperature of 100° C. during the course of 2 hours and by the action of a 1% solution of hydrochloric acid and an additional neutralization by of sodium hydroxide and evaporation of the solution to its dry state, a mixture of D-sodium glucuronate and sodium chloride is obtained. The precipitation of the D-sodium glucuronate from the mixture is accomplished by a multiple extraction using hot dimethyl sulphoxide and a later addition of acetone to the extract, as well as by filtering the precipitating D-sodium glucuronate.

The operational possibilities of the known method are limited to the use of 1,2-O-isopropylidene-D-glucuronic acid for metals, which produce insoluble chlorides, such as NaCl, in dimethyl sulphoxide. When the developing chlorides are soluble in dimethyl sulphoxide, the cleaning of the D-glucuronic acid salt by the extraction is not possible by using hot dimethyl sulphoxide.

One disadvantage of the known method is that during the neutralization and hydrolysis of the Na-isopropylidene glucuronic acid by hydrochloric acid as the result of the instability of the D-glucuronic acid, secondary conversions occur which reduce the yield and render the cleaning processes of the target products more complex. In addition, the cleaning of the Na salt of D-glucuronic acid leads to elaborate and environmentally harmful operating sequences for the extraction by dimethyl sulphoxide, and furthermore to a deposition of the product with acetone.

SUMMARY OF THE INVENTION

One object of this invention is to provide an environmentally friendly method of obtaining D-glucuronic acid which has widespread operational possibilities.

This object is achieved when, during the method of obtaining D-glucuronic acid in a water-containing solution in the presence of an oxygen agent, sulphonic acid cation exchanger resins are used as the oxygen agent.

The use of sulphonic acid cation exchanger resins, which have an exchange capacity of not less than 4 mg equ/g in a quantity of not less than 0.5 g relative to 0.001 mol of the salts of 1,2-O-isopropylidene-D-glucuronic acid, is optimum.

It is advantageous to accomplish the heating of the salts at temperatures of 40-95° C. A lower heating temperature significantly extends the process of hydrolysis, while a much higher temperature leads to a reduction in the yield of D-glucuronic acid because of the instability of this acid.

It is expedient to use, as the water-containing solution, a water solution formed from ethanol and having a concentration of not more than 50%, due to the poor solubility of the salts of isopropylidene glucuronic acid in ethanol. It is optimum to use alkali, alkaline-earth and ammonium salts as the salts of 1,2-O-isopropylidene-D-glueuronic acid, the cations of which salts are capable of combining with cation exchanger resins, such as Li, Na, K, Rb, Cs, Ca, Mg, Al, $NH_4$, and the like.

Currently, the inventors have ascertained, from information sources, no method for obtaining D-glucuronic acid within the scope of the present invention.

The method according to this invention is environmentally friendly and produces a purer product. The lack of homogeneous acid catalysts (HCi, oxalic acid and additional acids) in the solution prevents processes of secondary conversions of D-glucuronic acid, which processes contaminate the target products and require cleaning by labor-intensive and environmentally damaging technologies. The sulphonic acid cation exchanger resins, which are used as the acid agent, can be easily separated from the reaction mass by simple filtering and easily regenerated by known methods.

Ample operational possibilities of the method according to this invention are ensured when, in the method, any desirable salts of 1,2-O-isopropylidene-D-glucuronic acid are used, the cations of which are capable of combining with cation exchanger resins including alkali resins, alkaline-earth or ammonium salts, such as Li, Na, K, Rb, Cs, Ca, Mg, Al, $NH_4$, and the like.

With the method according to this invention, in a water-containing solution mainly in an alcoholic-aqueous solution, facilitates the removal of the solvents during the course of the precipitation of the GK and the GK lactone, because the addition of the low-boiling alcohol reduces the overall boiling temperature of the mixture of alcohol and water.

The technology of obtaining the D-glucuronic acid according to the method of this invention requires no significant outlay, because raw materials and reagent, such as glucose, water, alcohol, alkali, sulphocationite, mild conditions and a simplicity of the technological operations to be carried out (agitation, filtering, separating the solvent) can easily be obtained.

The use of cation exchanger resins during the production of D-glucuronic acid is known from Japan Pat. No. 15119, 1962, Chem. Abstr., 1963, Vol. 59, N 2136a; Japan Patent No. 1366, 1963, Chem. Abstr., 1964, Vol. 60, N 651a; Imai Y., Hirasaka Y., "Zakugaku Zasshi", 1960, Vol.80, Pages 1139-1142. However, these resins are only used in the processes of neutralising salts of D-glucuronic acid. According to this invention, besides neutralizing the salts of 1,2-O-isopropylidene-D-glucuronic acid during heating, the sulphonic acid cation exchanger resins ensure the separation (hydrolysis) of the protective isopropylidene group from said compounds.

In contrast to salts of 1,2-O-isopropylidene-D-glucuronic acid, the last hydrolytic function of the sulphonic acid cation exchanger resins is unclear. As known from the information sources, it has not been used earlier to obtain D-glucuronic acid.

During the hydrolysation and hydrolysis of the Na-isopropylidene-glucuronic acid with hydrochloric acid, sodium chloride is formed. When sulphonic acid cation exchanger resins are used, sodium chloride or other salts is or are missing, i.e. these solutions can be used, after the simple separation from the sulphonic acid cation exchanger resin, in various fields, such as the medicine and the food industry, as the direct source of D-glucuronic acid.

DESCRIPTION OF THE INVENTION

This invention is achieved with a mixture that is heated, which is formed from a salt of 1,2-O-isopropylidene-D-glucuronic acid, such as a calcium salt of 1,2-O-isopropylidene-D-glucuronic acid of the pentahydrate, a water-containing solution and a sulphonic acid cation exchanger resin, such as Amberlit-IR or KU-2 (universal cationite) which is produced by the "Azot" firm in Kemerowo.

Sulphonic acid cation exchanger resins are used which have an exchange capacity of not less than 4 mg equ/g in a quantity of not less than 0.5 g relative to 0.001 mol of the salts of 1,2-O-isopropylidene-D-glucuronic acid.

The heating is carried out at a temperature of 40-95° C. After the termination of the reaction, the cation exchanger resin is filtered and rinsed with water. The filtrate contains a mixture of D-glucuronic acid and D-glucuronic acid lactone. In the temperature range, the reaction occurs within 1-5 hours without secondary processes for decomposing the GK, so that an overall yield of the reaction products (sum of GK and GK lactone) is obtained. The ratio of GK and GK lactone in the product is only determined by the conditions of the thermodynamic equilibrium between them, the temperature and duration. A water solution, formed from ethanol and having a concentration of not more than 50%, is used as the water-containing solution. Alkali, alkaline-earth and ammonium salts are used as the salts of 1,2-O-isopropylidene-D-glucuronic acid, the cations of which are capable of combining with cation exchanger resins, e.g. Li, Na, K, Rb, Cs, Ca, Mg, Al, $NH_4$, and the like.

The removal of the D-glucuronic acid from the water or water-organic solution obtained is possible by many methods, such as through the neutralization of solutions formed from hydroxides of the alkali metals and obtaining of the respective salts of the D-glucuronic acid which, for its part, can be converted into a free D-glucuronic acid with the neutralization of the cation exchanger resins as taught by Japan Pat. No. 5119, 1962, Chem. Abstr., 1963, Vol. 59, N 2136a; Japan Patent No. 1366, 1963, Chem. Abstr., 1964, Vol. 60, N 651a, or with the processing of trifluoroacetic acid as taught by USSR No. 1089957, 1984 or with calcium or barium salts-GK with the treatment of sulphuric acid as taught by Mehltretter C. L., Alexander B. H., Mellies R. L. et al. "A Practical Synthesis of D-Glucuronic Acid through the Catalytic Oxidation of 1,2-isopropylidene-D-glucose", J. Am. Chem. Soc., 1951, V. 73, No. 6, Pages 2424-2427; Zervas L., Sessler P., "Ber. 1933" [in translation: "Report 1933"], Vol. 66, Pages 1326-1329; Ehrlich F., Rehorst K., "Ber. 1929" [in translation: "Report 1929"], Vol. 62A, Pages 628-634.

However, a direct use of the water and water-organic solutions of the GK and of the GK lactone obtained according to this invention as biologically active compounds is possible in cases when it is required without the direct removal of the D-glucuronic acid and GK lactone.

EXAMPLE 1

A mixture is heated at a temperature of 40° C. during a time period of 5 hours, which mixture comprises 3.88 g (0.00641 mol) calcium salt of 1,2-O-isopropylidene-D-glucuronic acid of the pentahydrate, 75 ml water and 14.8 g cation exchanger resin KU-2. The cation exchanger resin is filtered and rinsed with 10 ml water. The filtrate contains a mixture of D-glucuronic acid and D-glucuronic acid lactone in approximately the same ratio. Sodium hydroxide, having a pH value of 6.5-7, is supplied to the obtained solution at room temperature in a drop-wise manner by agitation. From the solution of sodium salt D-glucuronic acid obtained, water is removed at a temperature of not higher than 30° C. The residue is crystallized out of the ethanol-water (6:5) mixture. 1.23 g sodium salt D-glucuronic acid are obtained. The dilution of the mother solution with 96% ethanol still provides 0.33 g of the product. The total yield therefore amounts to 1.56 g (52%) of the pure sodium salt of the D-glucuronic acid of the crystal hydrate with a melting temperature of 147-149° C.

1.56 g sodium salt of the D-glucuronic acid of the crystal hydrate are dissolved in 10 ml water, then it is passed through a column which is filled with 10 g cation exchanger resin KU-2. The column is rinsed with water until a neutral reaction of the exchange water is obtained. From the solution of D-glucuronic acid obtained, water is removed at a temperature of not higher than 20° C. 1.26 g of crystallized D-glucuronic acid, 50% when converted into calcium salt of 1,2-O-isopropylidene-D-glucuronic acid of the crystal hydrate, are obtained.

EXAMPLE 2

A mixture is heated at a temperature of 95° C. for a time period of 1 hour, which mixture comprises 3.88 g (0.00641 mol) calcium salt of 1,2-O-isopropylidene-D-glucuronic acid of the pentahydrate, 75 ml water and 14.8 g cation exchanger resin KU-2.

The additional operations are carried out analogously to Example 1. 1.1 g crystallized D-glucuronic acid, 44% when converted into calcium salt of 1,2-O-isopropylidene-D-glucuronic acid of the pentahydrate, are obtained.

EXAMPLE 3

A mixture is heated at a temperature of 75° C. during a time period of 3 hours, which mixture comprises 3.88 g (0.00641 mol) calcium salt of 1,2-O-isopropylidene-D-glucuronic acid of the pentahydrate, 40 ml water, 40 ml 96% ethanol and 14.8 g cation exchanger resin KU-2. The cation exchanger resin is filtered and rinsed with 10 ml water. A solution of sodium hydroxide, having a pH value of 6.5-7, is added to the obtained solution at room temperature in a drop-wise manner by agitation. From the solution of sodium salt D-glucuronic acid obtained, water and ethyl alcohol are removed at a temperature of not higher than 30° C. The residue is crystallized out of the ethanol-water (6:5) mixture. The obtained sodium salt of D-glucuronic acid is dissolved in 10 ml water, then it is passed through a column which is filled with 10 g cation exchanger resin KU-2. The column is rinsed with water until the neutral reaction of the exchange water is obtained. From the solution of D-glucuronic acid obtained, water is removed at a temperature of not higher than 20° C. 1.23 g crystallized D-glucuronic acid, 49% when converted into calcium salt of 1,2-O-isopropylidene-D-glucuronic acid of the pentahydrate, are obtained.

EXAMPLE 4

A mixture is heated at a temperature of 75° C. during a time period of 3 hours, which mixture comprises 3.8 g (0.0128 mol) sodium salt of 1,2-O-isopropylidene-D-glucuronic acid, 75 ml water and 14.8 g cation exchanger resin KU-2. The cation exchanger resin is filtered and rinsed with 10 ml water. The filtrate contains a mixture of D-glucuronic acid and D-glucurone (lactone of D-glucuronic acid) in approximately the same ratio. The solution obtained is treated analogously to Example 1. 1.28 g crystallized D-glucuronic acid, 51.5% when converted into sodium salt of 1,2-O-isopropylidene-D-glucuronic acid, are obtained.

EXAMPLE 5

A mixture is heated at a temperature of 75° C. during a time period of 3 hours, which mixture comprises 3.88 g (0.00641 mol) calcium salt of 1,2-O-isopropylidene-D-glucuronic acid of the pentahydrate, 75 ml water and 15 g cation exchanger resin Amberlite IR-120. The cation exchanger resin is filtered and rinsed with 10 ml water. The filtrate is treated analogously to Example 1. 1.14 g crystallized D-glucuronic acid, 46% when converted into calcium salt of 1,2-O-isopropylidene-D-glucuronic acid of the pentahydrate, are obtained.

EXAMPLE 6

A mixture is heated at a temperature of 75° C. during a time period of 4 hours, which mixture comprises 3.88 g (0.00641 mol) calcium salt of 1,2-O-isopropylidene-D-glucuronic acid of the pentahydrate, 75 ml water and the cation exchanger resin KU-2 in a quantity of not less than its volume capacity (2.56 g). The additional operations are carried out analogously to Example 1. 1.03 g crystallized D-glucuronic acid, 41% when converted into calcium salt of 1,2-O-isopropylidene-D-glucuronic acid of the pentahydrate, are obtained.

The method according to the invention was successfully tested on an experimental scale by using charges of the reagent in a quantity of several hundred grams. The method of obtaining D-glucuronic acid according to this invention is environmentally friendly and has widespread operational possibilities.

Russian Patent Reference 2002108340 and PCT Patent Reference WO 03/082886, the priority documents corresponding to this invention, and their teachings are incorporated, by reference, into this specification.

What is claimed is:

1. A method of obtaining D-glucuronic acid by heating the salts of 1,2-O-isopropylidene-D-glucuronic acid in a water-containing solution in the presence of an acid agent wherein sulphonic acid cation exchanger resins are used as the acid agent and the water-containing solution includes ethanol wherein the ethanol is at a concentration of not more than 50%.

2. The method according to claim 1, wherein the sulphonic acid cation exchanger resins have a volume capacity of not less than 4 mg equ/g, in a quantity of not less than 0.5 g relative to 0.001 mol salts of 1,2-O-isopropylidene-D-glucuronic acid.

3. The method according to claim 1, wherein heating of the salts of 1,2-O-isopropylidene-D-glueuronic acid is accomplished at a temperature of 40-95° C.

4. The method according to claim 1, wherein salts of the alkali and one of alkaline-earth metal groups and ammonia salts are used as the salts of 1,2-O-isopropylidene-D-glucuronic acid.

* * * * *